US012718917B2

(12) United States Patent
Jain et al.

(10) Patent No.: US 12,718,917 B2
(45) Date of Patent: Aug. 25, 2026

(54) METHODS AND APPARATUSES FOR OPIOID OVERDOSE PREVENTION

(71) Applicants: Umang Jain, Fairfax, VA (US); Vyomika Jhilmil Gandhi, Aldie, VA (US); Justin Junseo Choi, McLean, VA (US)

(72) Inventors: Umang Jain, Fairfax, VA (US); Vyomika Jhilmil Gandhi, Aldie, VA (US); Justin Junseo Choi, McLean, VA (US)

(*) Notice: Subject to any disclaimer, the term of this patent is extended or adjusted under 35 U.S.C. 154(b) by 389 days.

(21) Appl. No.: 17/457,914

(22) Filed: Dec. 7, 2021

(65) Prior Publication Data

US 2023/0178201 A1 Jun. 8, 2023

(51) Int. Cl.

*G16H 20/10* (2018.01)
*A61J 7/00* (2006.01)
*A61M 37/00* (2006.01)
*G16H 40/63* (2018.01)

(52) U.S. Cl.

CPC ............ *G16H 20/10* (2018.01); *A61J 7/0076* (2013.01); *A61M 37/0015* (2013.01); *G16H 40/63* (2018.01); *A61M 2037/0023* (2013.01); *A61M 2205/18* (2013.01); *A61M 2205/3303* (2013.01); *A61M 2205/3553* (2013.01); *A61M 2205/50* (2013.01)

(58) Field of Classification Search

CPC ....... G16H 20/10; G16H 40/63; A61J 7/0076; A61M 37/0015; A61M 2037/0023; A61M 2205/18; A61M 2205/3303; A61M 2205/3553; A61M 2205/50

See application file for complete search history.

(56) References Cited

U.S. PATENT DOCUMENTS 4,662,537 A * 5/1987 Wolf .................... A61J 7/0481 221/89
8,920,375 B2 * 12/2014 Gonnelli ................ A61L 31/16 604/141
10,265,245 B2 * 4/2019 Kraft ...................... G16H 20/13
10,661,010 B1 * 5/2020 Tsinberg ........... A61M 5/14276
2007/0260491 A1 * 11/2007 Palmer .................. G16H 40/67 705/3

(Continued)

FOREIGN PATENT DOCUMENTS

CN 108671383 A * 10/2018 .......... A61B 5/4839
CN 110584633 A * 12/2019 .......... A61B 5/6802

(Continued)

OTHER PUBLICATIONS

CN108310615B—translated (Year: 2021).*

(Continued)

*Primary Examiner* — Jason S Tiedeman
*Assistant Examiner* — Jonathan C Edouard
(74) *Attorney, Agent, or Firm* — ArentFox Schiff LLP

(57) ABSTRACT

Methods and apparatuses for opioid overdose prevention are described. The apparatus comprises a memory and at least one processor coupled to the memory. The processor is configured to receive one or more measurements related to one or more vitals of a user, and cause, based on the one or more measurements, administration of a first dose of an overdose prevention medication to the user.

15 Claims, 13 Drawing Sheets

(56) References Cited

U.S. PATENT DOCUMENTS

| | | | | |
|---|---|---|---|---|
| 2009/0259176 | A1* | 10/2009 | Yairi | A61M 35/10 604/290 |
| 2011/0190702 | A1* | 8/2011 | Stumber | A61M 5/1723 604/151 |
| 2014/0155705 | A1* | 6/2014 | Papadopoulos | A61B 5/1112 600/301 |
| 2015/0048100 | A1* | 2/2015 | Dickie | G16H 40/60 221/1 |
| 2017/0172522 | A1* | 6/2017 | Insler | A61B 5/4845 |
| 2017/0213010 | A1* | 7/2017 | Sucilla | G16H 20/10 |
| 2019/0388667 | A1* | 12/2019 | Xu | A61N 1/0428 |
| 2020/0234811 | A1* | 7/2020 | Greenspan | A61J 7/0418 |
| 2021/0045972 | A1* | 2/2021 | Zuleta | A61J 7/0076 |
| 2021/0128078 | A1* | 5/2021 | Kiani | A61B 5/748 |
| 2021/0169410 | A1* | 6/2021 | Kassab | A61B 5/14735 |

FOREIGN PATENT DOCUMENTS

| | | | | |
|---|---|---|---|---|
| CN | 108310615 | B * | 6/2021 | A61M 37/0015 |
| JP | 6822031 | B2 * | 1/2021 | A61J 7/0084 |
| WO | WO-2016064266 | A2 * | 4/2016 | A61M 5/14244 |
| WO | WO-2021007344 | A1 * | 1/2021 | A61B 17/205 |
| WO | WO-2021016465 | A1 * | 1/2021 | A61B 5/14514 |

OTHER PUBLICATIONS

JP-6822031-B2-translated (Year: 2021).*
CN-108671383-A-translated (Year: 2018).*
CN-110584633-A-translated (Year: 2019).*

* cited by examiner

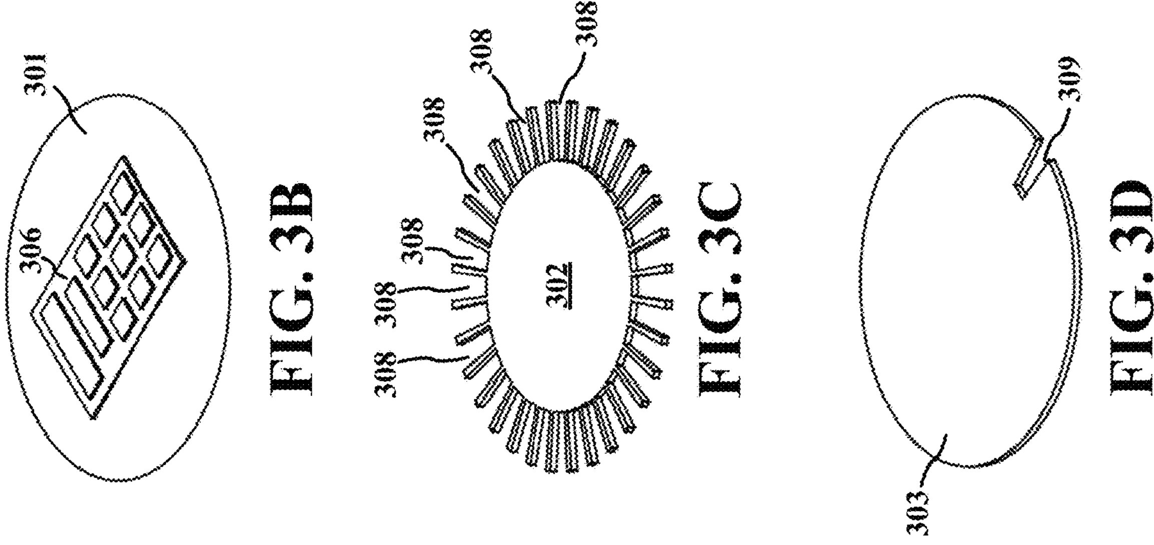
FIG. 3B
FIG. 3C
FIG. 3D
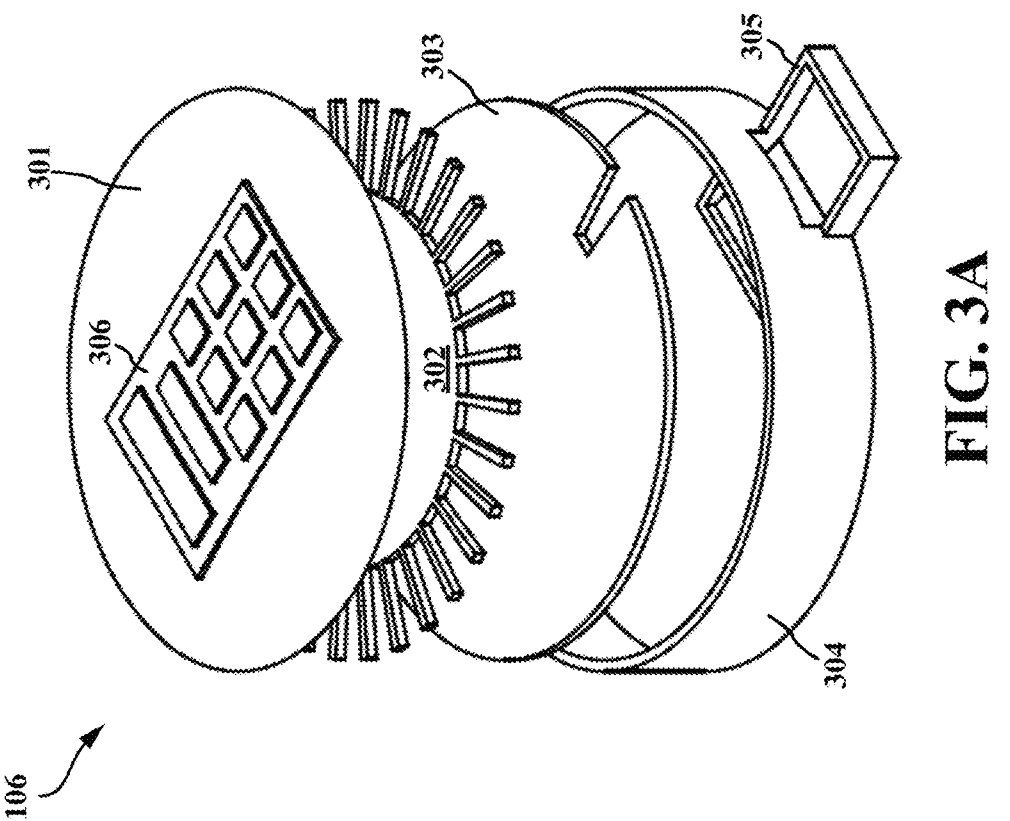
FIG. 3A

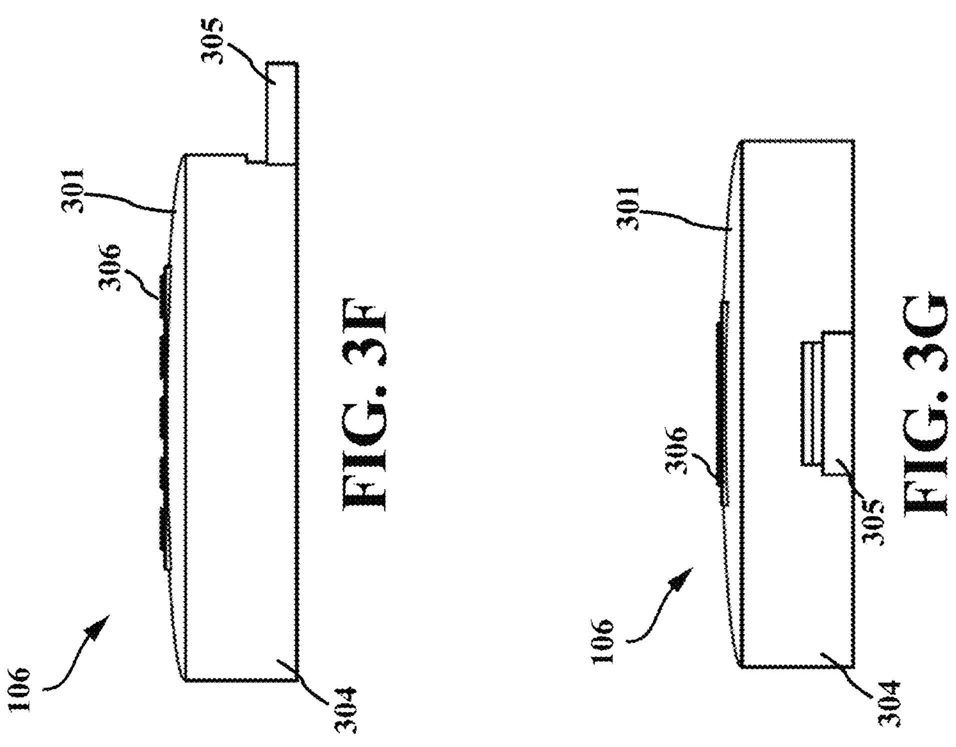
FIG. 3F
FIG. 3G
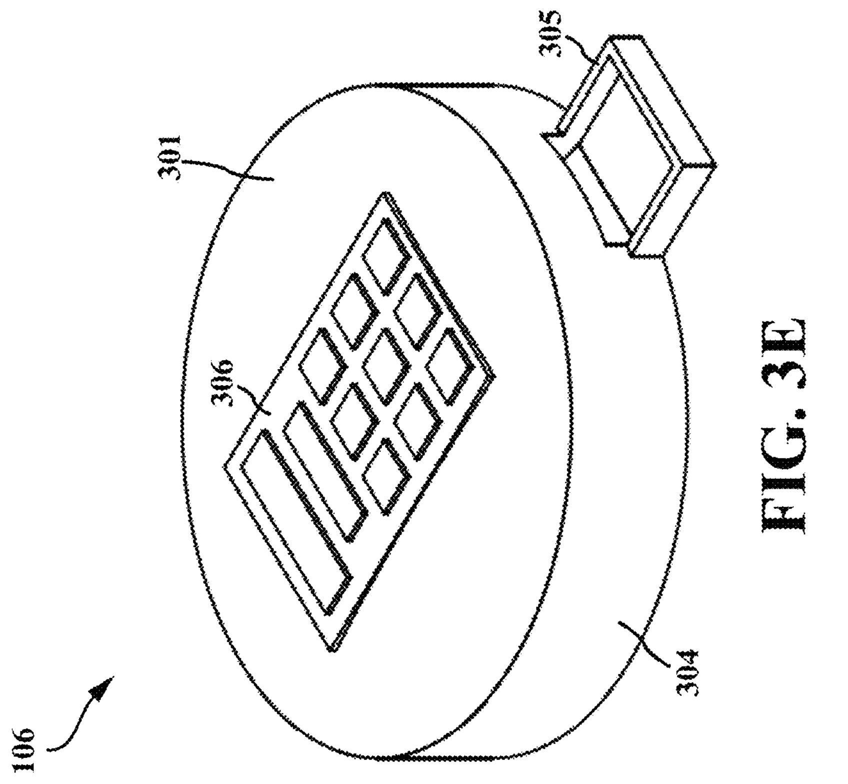
FIG. 3E

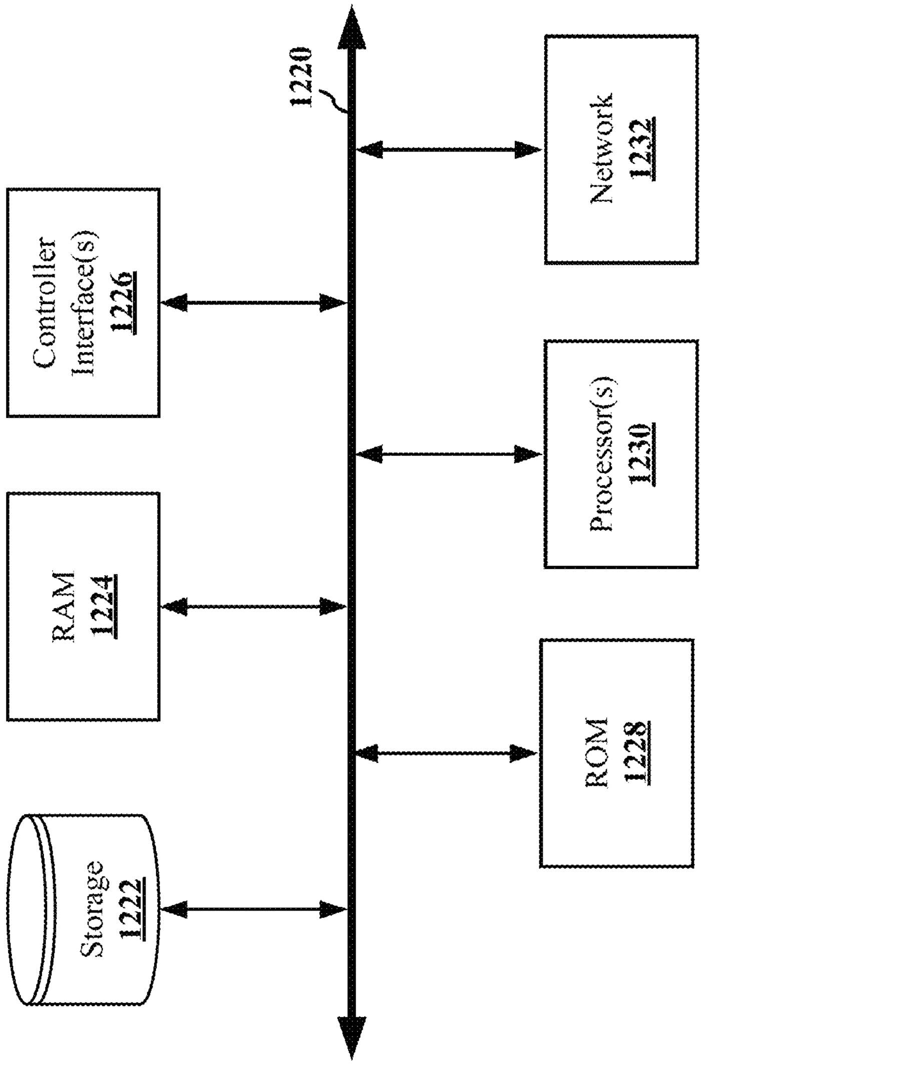
FIG. 12
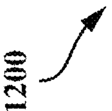

METHODS AND APPARATUSES FOR OPIOID OVERDOSE PREVENTION

BACKGROUND

Field

The present disclosure generally relates to patient monitoring, and more particularly, to techniques for opioid overdose.

Introduction

Overprescription of opioid medications for years has led to an epidemic of opioid abuse and has grown into a major health crisis all over the world. Patients are generally introduced to opioids through prescription medication prescribed by their doctors for managing pain resulting from a physical injury. Over time, a large number of these patients may become addicted to the opioids while also building a tolerance to the opioids. This vicious cycle results in these patients taking more of the opioids to satisfy their addiction and eventually overdosing on the opioids.

Existing systems and techniques may monitor a patient's vitals and may contact emergency medical services (EMS) when the patient's vitals fall below a certain threshold level. This generally results in the EMS arriving at the patient's location and attempting to save the patient. However, contacting the EMS may not save the patient's life because the patient may suffer from any number of fatal physiological injuries (e.g., brain damage) by the time the EMS reaches the patient. Therefore, existing monitoring systems and techniques fail to prevent a patient's death with a high probability of success. To make matters worse, such monitoring systems may even provide a false sense of security to the patients, their families, and their doctors about the monitoring systems ability to save the patients' lives.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

Over the past several years, opioid addiction and overdose has become a major health crisis all over the world. A large number of people that suffer from opioid addiction and those who die from opioid overdose are initially introduced to opioids through prescription medications from a doctor that treated that person for an injury. Generally, these patients do not have a history of substance abuse. Therefore, with appropriate prevention systems a large number of such patients can avoid being addicted to opioids. However, existing prevention systems continue to fail to incorporate sufficient safeguards that can successfully prevent a large number of patients that are prescribed opioid medications from being addicted and/or overdosing on opioid medications.

Therefore, the present disclosure describes various techniques and solutions for opioid overdose prevention that address the various deficiencies of the existing systems. According to the techniques and solutions described herein, credentials of a user (e.g., a patient) are provided to an application being executed on a computing device (e.g., a mobile computing device, a smartphone, a tablet, and the like), where the application is configured to determine whether the user credentials are valid. In response to determining, the user credentials are valid, the application may be configured to generate a code to unlock a medication dispenser. The medication dispenser dispenses prescribed amount of medication in response to receiving the correct generated code. Furthermore, the techniques and solutions described herein allow for measurements of vitals of a user, and based on the vitals of the user, determine whether the user is overdosing. In response to determining that the user is overdosing, the techniques and solutions described herein allow for autonomous administration of a dose of an antidote to the overdose. The techniques and solutions described herein further allow for continuous monitoring of the patient vitals after the administration of the first dose of the antidote, and autonomously administer another dose of antidote based on the vitals of the user after the administration of the first dose. The techniques and solutions described herein also allow for emergency providers to be autonomously and concurrently contacted if any of the vitals of the user fail to satisfy corresponding threshold vital levels. Such techniques and approaches may be enabled through various apparatuses, systems, methods, and/or computer-readable media described herein.

In some embodiments of the present disclosure, a method for generating a code to unlock a medication dispenser is described. The method of generating a code to unlock a medication dispenser comprises receiving credentials of user at a first time. The method further comprises determining whether the user is a valid user, based on the received credentials. The method further comprises generating a code to unlock a medication dispenser, in response to determining that the user is a valid user. The method further comprises causing the generated code to be displayed on a display device.

In some embodiments, a method for administering a dose of an antidote to a user is described. The method of administering a dose of an antidote to a user comprises measuring, at a health monitoring device, one or more vitals of a user. The method further comprises transmitting, at the health monitoring device, one or more messages comprising the one or more vitals to a mobile device associated with the user. The method further comprises receiving, at the health monitoring device, a message from the mobile device to administer a dose of an overdose prevention medication to the user, in response to the one or more messages transmitted to the mobile device. The method further comprises administering, at the health monitoring device, based on the received message, a dose of the antidote to the user.

In some embodiments, a method for dispensing a prescribed amount of medication for a user is described. The method for dispensing a prescribed amount of medication comprises receiving, at a medication dispenser, a code generated by a mobile computing device. The method further comprising determining whether the received code is a valid code. The method further comprising dispensing a prescribed amount of medication for a user in a tray of the medication dispenser in response to determining that the received code is a valid code.

It will be understood that other aspects of generating a code to unlock a medication dispenser, administering a dose of an antidote to a user, and/or dispensing a prescribed amount of medication will become readily apparent to those skilled in the art from the following detailed description, wherein it is shown and described in several embodiments by way of illustration. As will be realized by those skilled in the art, the disclosed subject matter is capable of other and different embodiments and its several details are capable of modification in various other respects, all without departing from the present disclosure. Accordingly, the drawings and detailed description are to be regarded as illustrative in nature and not as restrictive. To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

FIG. 2A illustrates a perspective exploded view of a health monitoring device, in accordance with some embodiments of the present disclosure.

FIG. 2B illustrates a side perspective view of a health monitoring device, in accordance with some embodiments of the present disclosure.

FIG. 2C illustrates a top perspective view of a health monitoring device, in accordance with some embodiments of the present disclosure.

FIG. 2D illustrates a perspective view of a health monitoring device, in accordance with some embodiments of the present disclosure.

FIG. 3A illustrates a perspective exploded view of a medication dispenser, in accordance with some embodiments of the present disclosure.

FIG. 3B illustrates a top component of a medication dispenser, in accordance with some embodiments of the present disclosure.

FIG. 3C illustrates a wheel of a medication dispenser, in accordance with some embodiments of the present disclosure.

FIG. 3D illustrates an intermediate layer of the medication dispenser, in accordance with some embodiments of the present disclosure.

FIG. 3E, illustrates a perspective view of a medication dispenser, in accordance with some embodiments of the present disclosure.

FIG. 3F illustrates a side perspective view of a medication dispenser, in accordance with some embodiments of the present disclosure.

FIG. 3G illustrates a front perspective view of a medication dispenser, in accordance with some embodiments of the present disclosure.

FIG. 12 is a block diagram of an example processing system configured to execute one or more sets of instructions of example apparatuses, in accordance with some embodiments of the present disclosure.

DETAILED DESCRIPTION

The detailed description set forth below in connection with the appended drawings is intended to provide a description of various exemplary embodiments and is not intended to represent the only embodiments in which the invention may be practiced. The term "exemplary" used throughout this disclosure means "serving as an example, instance, or illustration," and should not necessarily be construed as preferred or advantageous over other embodiments presented in this disclosure. The detailed description includes specific details for the purpose of providing a thorough and complete disclosure that fully conveys the scope of the invention to those skilled in the art. However, the invention may be practiced without these specific details. In some instances, well-known structures and components may be shown in block diagram form, or omitted entirely, in order to avoid obscuring the various concepts presented throughout this disclosure. In addition, the figures may not be drawn to scale and instead may be drawn in a way that attempts to most effectively highlight various features relevant to the subject matter described.

Figure 1:
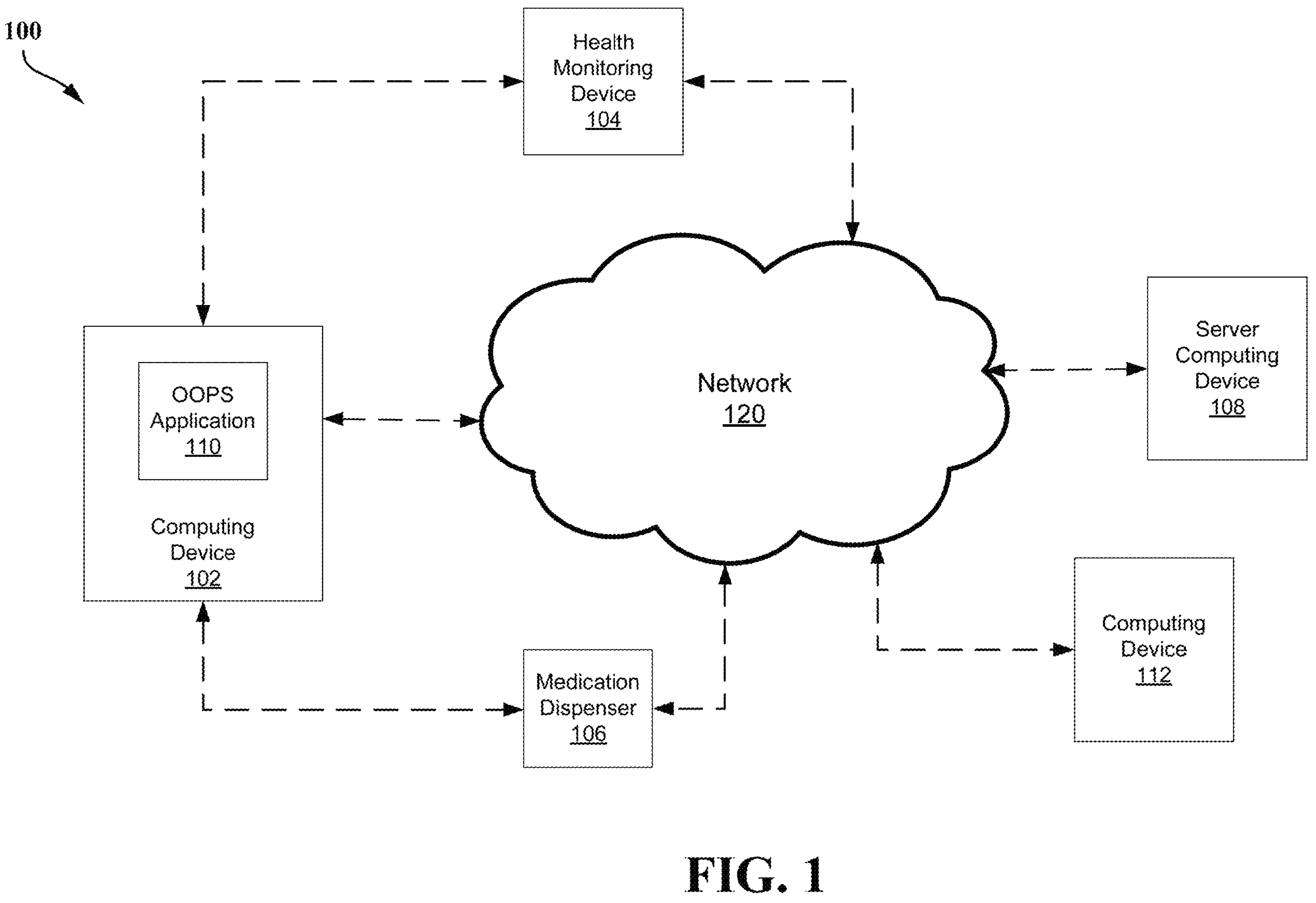
FIG. 1 illustrates a network arrangement of the opioid overdose prevention system, in accordance with some embodiments of the present disclosure.

Referring now to FIG. 1, there is shown an example network arrangement of an opioid overdose prevention system 100, referred to herein as the "system 100." The system 100 may include a computing device 102, a health monitoring device 104, a medication dispenser 106, and a server computing device 108. Examples of the computing device 102 may include, but are not limited to, a mobile computing device, a smartphone, a tablet, and the like. The computing device 102 may be configured to communicate with one or more other computing devices. For example, the computing device 102 may be configured to connect with a communications network and communicate with another computing device connected to that communication network using a communication protocol associated with the communication network.

As shown in FIG. 1, as an example, the computing device 102 may be communicatively coupled to a health monitoring device 104, the medication dispenser 106, and the server computing device 108. In some implementations, as shown in FIG. 1, the computing device 102 may be communicatively coupled to the health monitoring device 104. In some implementations, the computing device 102 may be communicatively coupled to the health monitoring device 104 via a wireless personal area network technology, such as Bluetooth, Bluetooth low energy, and the like, and communicate with each other using a communication protocol of the wireless personal area network. Similarly, the computing device 102 may be communicatively coupled to the medication dispenser 106 and the server computing device 108 via communications network 120. The communications network 120 may be a local area network (LAN), a wide area network (WAN), the Internet, a remote or cloud server, and the like, and the computing device 102, the medication dispenser 106, and/or the server computing device 108 may communicate with each other using associated communication protocols (e.g., Wi-Fi, cellular, and the like).

The health monitoring device 104 may be configured to acquire and/or monitor information related to the vitals of the user and may be worn around a portion of the user's body. For example, the health monitoring device 104 may be worn around a wrist of the user. Similarly, the health monitoring device 104 may be worn around a thigh of the user. The health monitoring device 104 may comprise one or more sensors 210, as shown in FIG. 2, which are configured to use photoplethysmography techniques to acquire information related to the user's heart rate and/or respiratory rate. For example, one of the sensors 210 may be configured to emit infrared light towards the user, and another sensor 210 may be configured to receive infrared light reflected back from the user, and based on the changes in the intensity of the infrared light, the sensors 210 may determine the user's heart rate and/or respiratory rate.

In some implementations, the sensors 210 may be configured to transmit the user's heart rate and/or respiratory rate to a processor (not shown separately) of the health monitoring device 104. The processor of the health monitoring device 104 may be configured to transmit the user's heart rate and/or respiratory rate to the computing device 102. In some implementations, the sensors 210 may be configured to transmit the user's heart rate and/or respiratory rate to the computing device 102. The sensors 210 may be located on an underside 202 of the health monitoring device, as shown in the top perspective view of FIG. 2C.

The health monitoring device 104 may include one or more microneedle patches, such as microneedle patches 212*a*, 212*b*, 212*c*, collectively referred to herein as microneedle patches 212. Each of the microneedle patches 212 may store a dose of an antidote medication to counter and/or reverse any overdosing of the prescribed medication stored in the medication dispenser 104. In some implementations, the antidote medication may be naloxone. The amount of antidote medication stored in each microneedle patch 212 may be predetermined. The microneedle patches 212 may be located on the underside 202 of the health monitoring device 104. Each of microneedle patches 212 may be electrically and/or communicatively coupled (e.g., via a wire) to the processor of the health monitoring device 104. The processor of the health monitoring device 104 may be configured to actuate a non-empty microneedle patch 212 to cause the microneedle patch 212 to penetrate the skin of the user and administer the dose of the antidote subcutaneously into the user. In some implementations, one or more microneedle patches may be removed from the heath monitoring device 104 and replaced with another microneedle patch. For example, a microneedle patch 212 may be empty after administration of the stored antidote, and such an microneedle patch 212 may be removed and replaced with a microneedle patch 212 storing a full dose of the antidote.

The health monitoring device 104 may be configured with a power supply. For example, the health monitoring device 104 may include a battery configured to supply power to one or more components of the health monitoring device 104, such as sensors 210, processor of the health monitoring device 104, and the like.

Figures 2A, 2B, 2C, 2D:
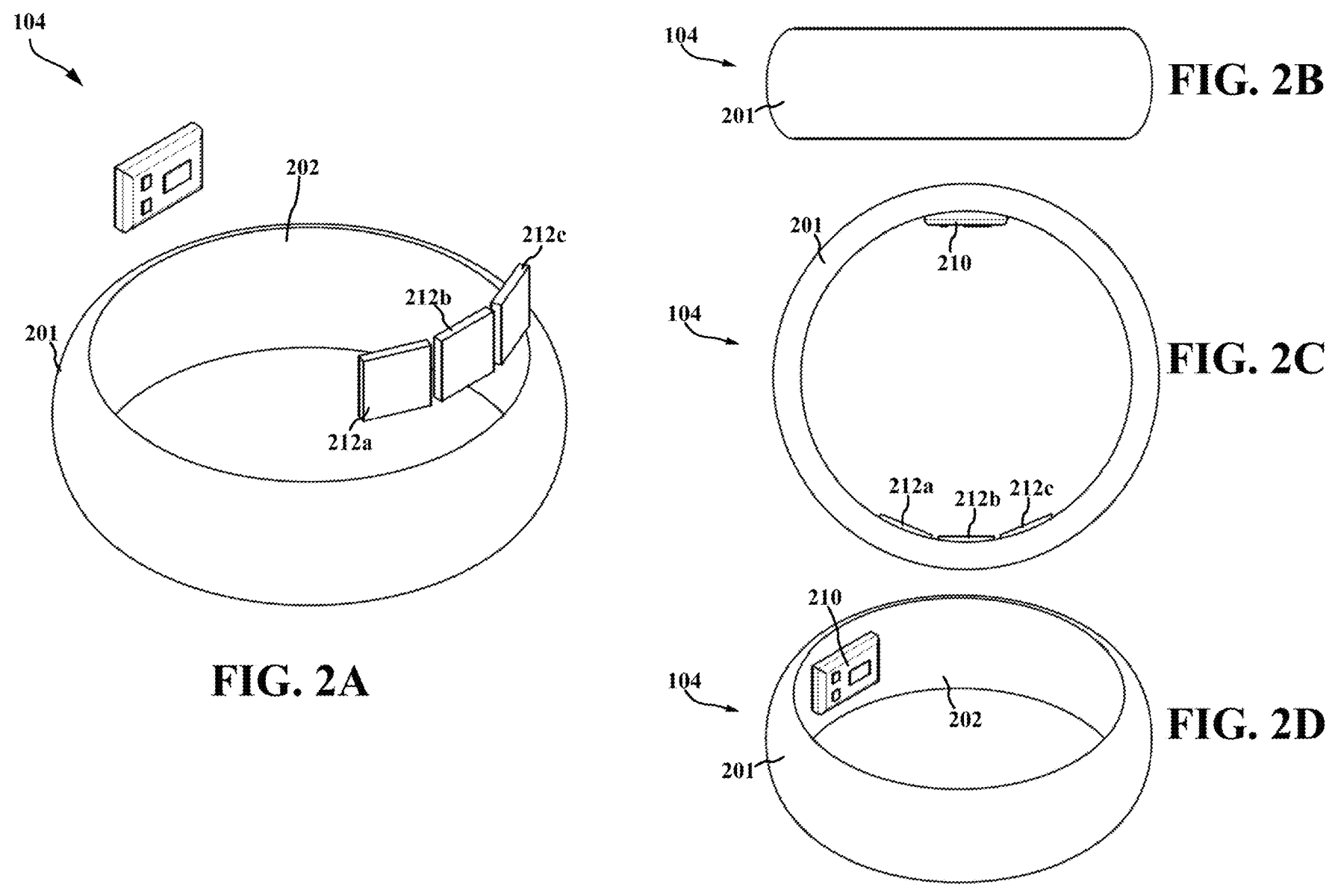

In some implementations, as shown in FIG. 2A, the health monitoring device 104 may be configured as a bracelet. The band 201 of the health monitoring device 104 may be constructed out of various materials that have viscosity, elasticity, a high failure strain, and the like. For example the band 201 may be constructed out of elastomer. In some implementations, the band 201 may have a thickness of 0.7 centimeters (cm), a diameter of 6 cm, a height of 2 cm. In some implementations, each of the one or more sensors 210 may have a length of 1 cm, a width of 1.5 cm, and a height of 0.25 cm. In some implementations, each of the microneedle patches 212 may be a square, where the size of a side of the microneedle patch may be 1 cm, and a thickness of 0.15 cm. In some implementations, a height of the band 201 may be large enough (e.g., 2 cm) such that the various components (e.g., sensors 210, microneedle patches 212, and the like) of the health monitoring device 104 may be located full within the band 201. For example, the various components of the health monitoring device 104 may not be visible from certain perspective views, such as a side perspective view, as shown in FIG. 2B.

The medication dispenser 106 may comprise a top component 301, a wheel 302, an intermediate layer 303, a base 304, a tray 305, a keypad 306, as shown in the exploded perspective view of FIG. 3A. The top component 301 may provide a top enclosure for medication dispenser 106 as shown in FIGS. 3E-3G. The keypad 306 may be part of the top component 301 as shown in FIGS. 3A, 3B, 3E-3G. In some implementations, the keypad 306 may be communicatively connected to a processor of the medication dispenser 106 and the keypad 306 may transmit a code entered using the keypad 306 to the processor of the medication dispenser 106 for authenticating the code. In some implementations, the top component 301 may have a diameter of 130 millimeters (mm) and a thickness of 6 mm. In some implementations, the keypad 306 may have a length of 75 mm and a width of 50 mm.

The wheel 302 may be configured to be rotatable around a vertical axis. The wheel 302 may include multiple slots 308 to store the prescribed medication. In some implementations, the size of a side of each slot 308 may be 20 mm. The wheel 302 may be connected to the top component 301 and the intermediate layer 303 at a central axis of the wheel 302. The intermediate layer 303 may be solid with an opening at portion of the intermediate layer 303, as shown in FIG. 3D. The size of the opening of the intermediate layer 303 may be the same as the size of the slot 308. The intermediate layer 303 may be connected to the base 304 such that the opening of the intermediate layer 303 may align with the tray 305 of the base 304. In some implementations, the tray may have a width of 35 mm and a length of 50 mm. In some implementations, a portion of the tray 305 may be located outside of the base 304 as shown in FIGS. 3A, 3E-3G. For example, half a length of the tray 305 may be located outside of the based 304.

The medication dispenser 106 may include a motor (not shown separately), which may be connected to the wheel 302. The motor of the medication dispenser 106 may be configured to rotate the wheel 302 around the vertical axis. The motor of the medication dispenser 106 may be electrically and/or communicatively coupled with a processor of the medication dispenser 106. In response to receiving a valid code via the keypad 306, the processor of the medication dispenser 106 may be configured to turn on the motor and cause the wheel 302 to rotate until a slot 308 of the wheel 302 aligns with the opening of the intermediate layer 303, which causes the medication stored in the slot 308 to be dispensed into the tray 305. A perspective view of the fully assembled medication dispenser 106 is shown in FIG. 3E. FIGS. 3F and 3G show a side and a front perspective views, respectively, of the medication dispenser 106.

Returning to FIG. 1, the computing device 102 may comprise a memory configured to store instructions, which when executed by a processor of the computing device 102 execute various applications, modules, functionalities, techniques, and/or solutions described herein. The computing device 102 may be configured to execute various applications including, but not limited to, Opioid Overdose Prevention System (OOPS) application 110. The OOPS application 110 may be configured to receive credentials of a user via an input device (not shown separately) of the computing device 102. The input device 102 may include, but is not limited to, a touch screen display, an image capturing device, a keyboard, and the like. In some implementations, the credentials of the user may be biometric information of the user, such as a facial image, a finger print, and the like. In some implementations, the credentials of the user may be a username and password associated with the user.

The OOPS application 110, via the processor of the computing device 102, may be configured to determine whether the received credentials of the user are authorized for accessing the OOPS application 110. In response to the OOPS application 110 determining that received user credentials are valid and/or authorized to access the OOPS application, the OOPS application 110, via the processor of the computing device 102, may generate a code to unlock the medication dispenser 106. In some implementations, the OOPS application 110 may generate the code to unlock the medication dispenser 106 after receiving a request to generate the code. For example, a user that successfully logs into the OOPS application 110 may provide a request to generate the code via a graphical user interface (GUI) of the OOPS application 110. The OOPS application 110, via the processor of the computing device 102, may cause the generated code to be displayed to a display device (e.g., a display device of computing device, and the like).

In some implementations, the OOPS application 110 may be configured to determine one or more time periods at which the prescribed medication has been dispensed in over a previous number of days, and deny generating a code to unlock the medication dispenser if the current time at which a request for the code is received is outside the one or more time periods. For example, the OOPS application 110 may determine that the user has requested medication to be dispensed or a code to unlock the medication dispenser 106 between 10 and 10:30 am, and the OOPS application 110 may deny generation of the code if the current time is outside the range of time between 10 and 10:30 am.

In some implementations, the OOPS application 110 may be configured to store the number of times a prescribed medication has been dispensed within a predetermined amount of time (e.g., a day, 24 hours, and the like). In some implementations, the OOPS application 110 may be configured to deny generating a code to unlock the medication dispenser 106 if the number of times the prescribed medication has been dispensed satisfies the total number of times that the user must consume the medication within a predetermined amount of time (e.g., single day, a certain number of hours, and the like). For example, if a user is prescribed to only consume the medication twice within a single day, and the OOPS application 110 determines that medication was already dispensed twice today, then the OOPS application 110 may deny generating the code for the medication dispenser 106.

The OOPS application 110 may be configured to transmit, via the computing device 102, the user's health data (e.g., heart rate, respiratory rate, and the like) received from health monitoring device 104 to the server computing device 108. The OOPS application 110 may be configured to encrypt the user's health data prior to transmitting it to the server computing device 108. The OOPS application 110 may encrypt the user's health data using any of the encryption algorithms and/or techniques including, but not limited to, GnuPG, SHA-252, and the like. In some implementations, the OOPS application 110 may use a distributed ledger (e.g., a blockchain) to store the user's health data. The OOPS application 110 may be configured to implement various user authentication procedures to determine whether a user should be granted access to the application.

Figure 4:
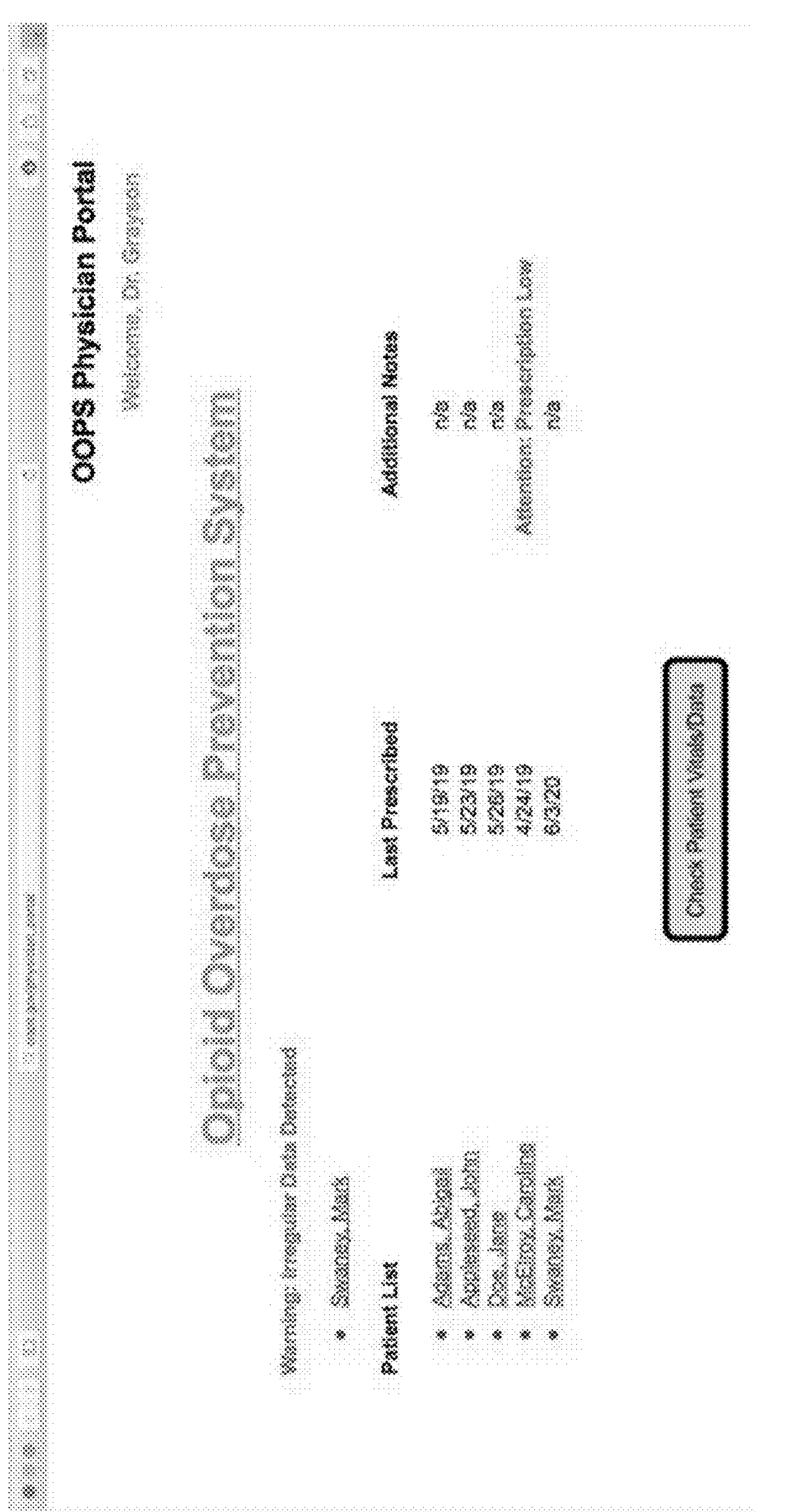
FIG. 4 illustrates an example graphical view of a user interface of a physician portal, in accordance with some embodiments of the present disclosure.

The OOPS application 110 may be configured to provide a physician's portal for physicians that prescribe medication to the users of the OOPS application 110. For example, if a physician enters the OOPS application 110 using his or her physician credentials and not his or her user credentials, then the OOPS application may be configured to provide them with a graphical interfaces that are configured to allow the physician to view information related his or her patients (e.g., users of the OOPS application 110). In some implementations, the physician's portal of the OOPS application 110 may be a website which the physician accesses using his or her physician credentials granted by the OOPS application. An example GUI of a web based physician's portal is shown in FIG. 4. As shown in FIG. 4, the physician upon logging into the physician's portal may be shown a list of his or her patients, the last time they were prescribed their medications, any notes related to the prescribed medications, highlight any patients experiencing any irregularities (e.g., heart rate irregularities, respiratory rate irregularities, and the like), and other similar attributes and/or notes related to the patients. The physician's portal may also be configured to view more detailed information related to each and/or all of the physician's patients, for example, by clicking a graphical item, such as the patient's name, and/or a graphical button as shown in FIG. 4.

Figure 5:
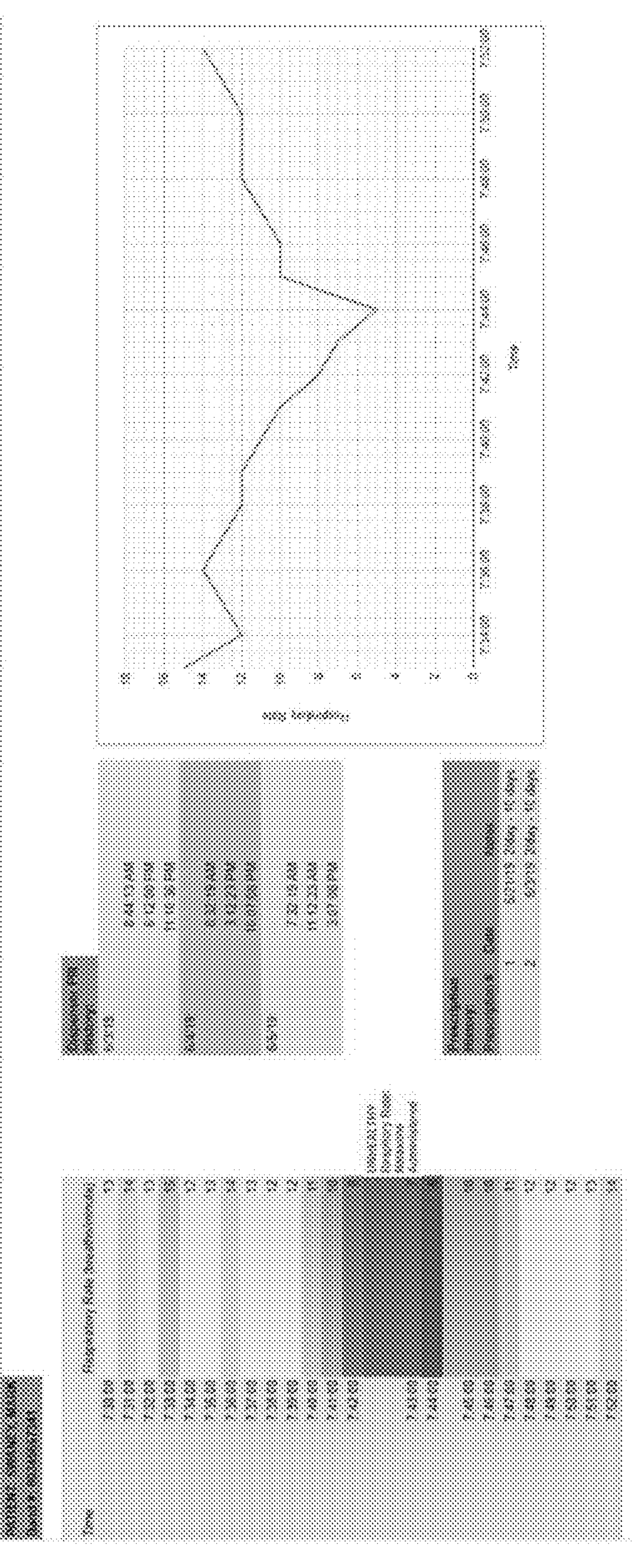
FIG. 5 illustrates another example graphical view of a user interface of a physician portal, in accordance with some embodiments of the present disclosure.

For example, as shown in FIG. 5, upon clicking the patient "Swaney, Mark," the physician's portal may display a new graphical page that displays a history of the health data of that patient, such as a respiratory rate of the patient over the last hour, few hours, days, and the like. Similarly, the physician's portal may provide the medication dispensation and/or consumption history of the patient, the medication prescription history, one or more charts that graphically depict respiratory rate of the patient over a certain period of time, as shown in FIG. 5.

Figure 6B:
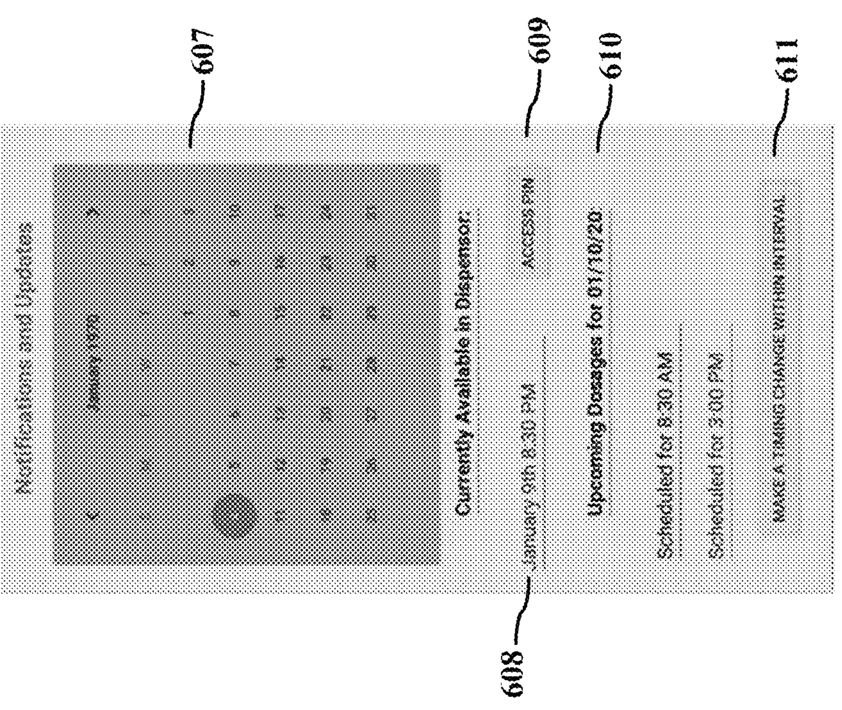
FIG. 6B illustrates another example graphical of user interface for a patient and/or user, in accordance with some embodiments of the present disclosure.
Figure 6A:
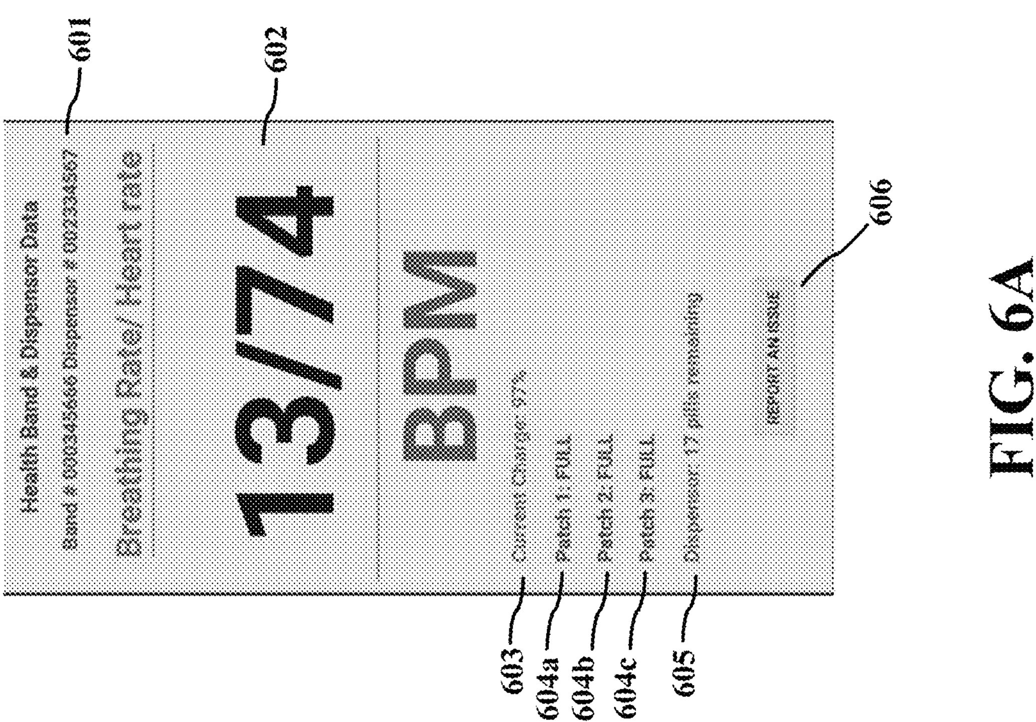
FIG. 6A illustrates an example graphical view of user interface for a patient and/or user, in accordance with some embodiments of the present disclosure.

The OOPS application 110 may present GUIs to the patients and/or users of the OOPS application 110 that may be different from the GUIs displayed to physicians. Example GUIs provided to the patients and/or user of the OOPS application 110 are shown in FIG. 6A and FIG. 6B. In some implementations, the OOPS application 110 may present to the user information that identifies the health monitoring device 104 and/or the medication dispenser device 106 that are communicatively coupled and/or connected to the OOPS application 110. For example, in FIG. 6A, graphical element 601 indicates to the user identifiers of the communicatively coupled and/or connected health monitoring device 104 (e.g., "Band #000345666") and medication dispenser 106 (e.g., Dispenser #002334567) to the user.

The GUI of the OOPS application 110 may be configured to present to the user information received from the health monitoring device. For example, as shown by graphical element 602 in FIG. 6A, the GUI of the OOPS application 110 may present data related to one or more vitals of the user, such as the breathing rate and heart rate of the user.

Similarly, as shown in FIG. 6A, the GUI of the OOPS application 110 may present information related to the operational status of the health monitoring device 104, such as the current battery charge level of the health monitoring device 104, as indicated by the graphical element 603, and the current medication levels of each of the microneedle patches of the health monitoring device 104, as indicated by the graphical elements 604*a*, 604*b*, 604*c*.

In some implementations, the GUI of the OOPS application 110 may present information received from the medication dispenser 106. For example, based on the number of times the prescribed amount of medication was successfully dispensed and the total amount of prescribed medication stored in the medication dispenser 106, the processor of the medication dispenser may be configured to calculate the amount of medication remaining in the medication dispenser 106 and cause that information to be transmitted and/or transmit that information to the computing device 102 and/or the OOPS application 110 hosted on the computing device 102. The OOPS application 110 may present to the user, via a graphical element on the GUI, such as graphical element 605 of FIG. 6A, the information received from the medication dispenser 106. In some implementations, the GUI of the OOPS application 110 may be configured to present graphical elements that are configured to contact and/or transmit alerts or messages to another party, personnel, and the like. For example, the GUI of the OOPS application 110 may be configured to allow the user to transmit a message to a help desk or support line via interaction with the graphical element 606.

The GUI of OOPS application 110 may be configured to present to the user a schedule of when the user may be expected and/or prescribed to consume the prescribed medication. For example, as indicated by graphical element 608 in FIG. 6B, the GUI of the OOPS application 110 may indicate the immediate next prescribed time to access and consume the medication. Similarly, as indicated by graphical elements 610 in FIG. 6B, the GUI of the OOPS application 110 may also indicate upcoming times at which the user is expected to and/or prescribed to consume the medication. In some implementations, the GUI of the OOPS application 110 may be configured to allow the user to change the times at which to consume the prescribed medication. For example, graphical element 611 may be configured to update the medication consumption times. In some implementations, as indicated by graphical element 607 in FIG. 6B, the GUI of the OOPS application 110 may present an interactive calendar to the user. In some implementations, the GUI may allow the user to access the prescribed medication times on different days to view and/or update any corresponding medication times on those days.

The GUI of the OOPS application 110 may also include graphical elements configured to generate access codes for the medication dispenser. For example, graphical element 609 in FIG. 6B may be configured to be interacted (e.g., clicking, touching, and the like) by the user, and interaction with the graphical element 609 may cause generation of an access code for the medication dispenser 106 if other conditions for generation of the access code described herein are satisfied. In some implementations, the graphical element 609 may be configured to be operable when the current time satisfies a threshold amount of time relative to the prescribed and/or schedule medication time. For example, the threshold amount of time may be 1 minute before the next prescribed and/or scheduled medication time (e.g., the time indicated by the graphical element 608), and the graphical element 609 may only become operable if the current time satisfies the threshold amount of time (e.g., within 1 minute of the time indicated by the graphical element 608). In some implementations, the graphical element 609 may be configured to become inoperable once a valid code for the medication dispenser 106 is generated and it may be configured to remain inoperable until the next prescribed and/or scheduled medication time and/or any threshold amount of time until the next prescribed and/or scheduled medication time.

Figure 7:
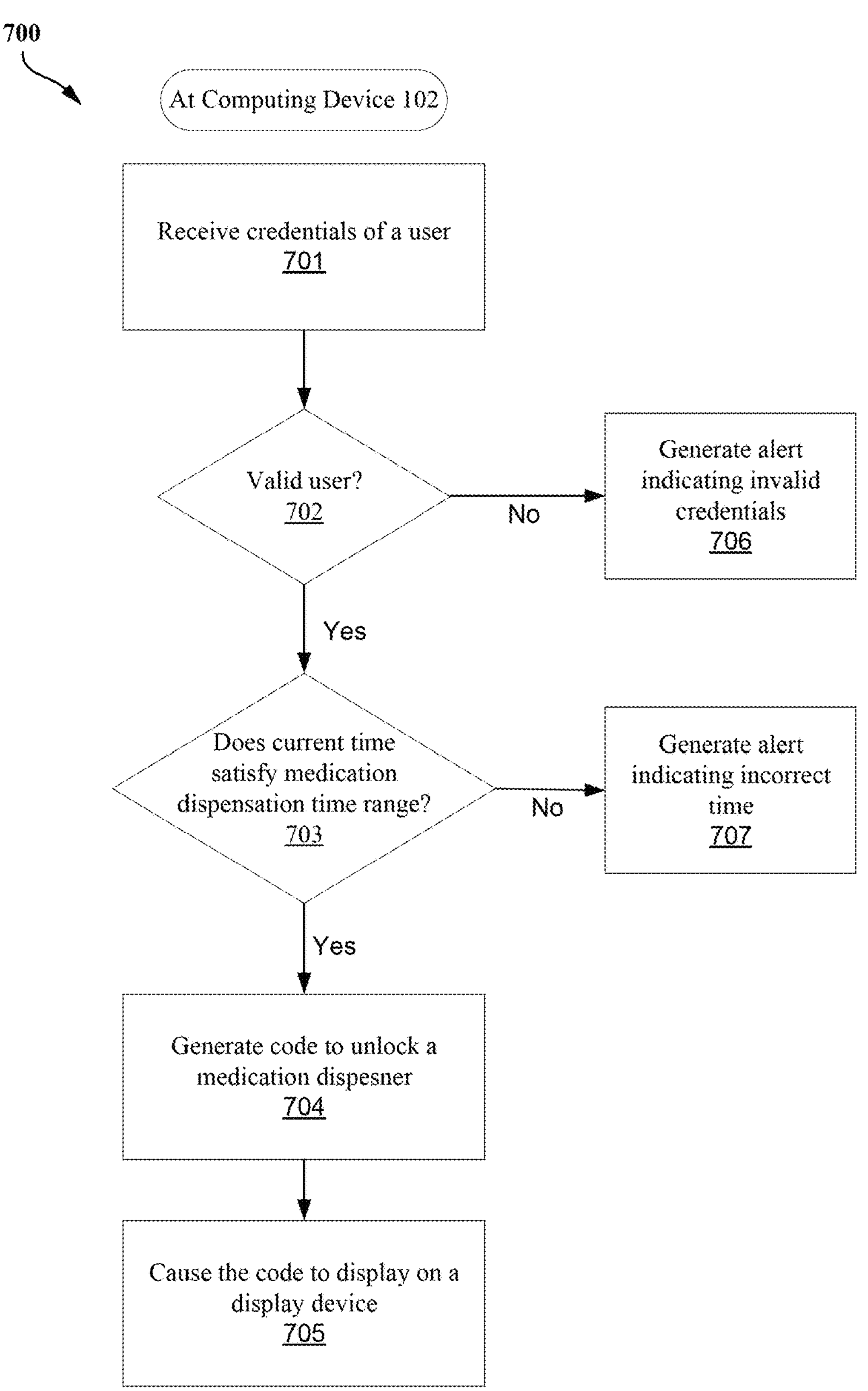
FIG. 7 illustrates a flowchart of an example method for generating a code for unlocking a medication dispenser, in accordance with some embodiments of the present disclosure.

Turning now to FIG. 7, there is shown an example method 700 for generating a code for unlocking a medication dispenser. The example process may be implemented at a computing device 102, and can be performed using one or more components (e.g., a processor, a memory, and the like) of the computing device 102.

At block 701, a processor of the computing device 102 receives credentials of a user. For example, via the OPPS application 110 executed on the computing device 102, a processor of the computing device 102 may receive the credentials of the user. At block 702, a processor of the computing device 102 determines whether the user is a valid user, for example, by comparing the entered credentials with credentials stored for that username. If the processor of the computing device 102 determines that the user is not valid ("No" at block 702), then the method 700 proceeds to block 706, and the processor of the computing device 102 generates an alert indicating that the credentials are invalid. The processor of the computing device 102 may cause the generated alert to be displayed on a display device of the computing device 102. If the processor of the computing device 102 determines that the user is valid ("Yes" at block 702), then the method 700 proceeds to block 703.

At block 703, the processor of the computing device 102 determines whether the current satisfies medication dispensation time range. If the processor of the computing device 102 determines that the current time fails to satisfy the medication dispensation time range ("No" at block 703), then the method 700 proceeds to block 707, and the processor of the computing device 102 generates an alert indicating that the current time is outside of the time that the user generally consumes his or her medication. The processor of the computing device 102 may cause the generated alert to be displayed on a display device of the computing device 102. If the processor of the computing device 102 determines that the current time fails to satisfy the medication dispensation time range ("No" at block 703), then the method 700 proceeds to block 704.

At block 704, the processor of the computing device 102 generates a code to unlock a medication dispenser (e.g., medication dispenser 106). At block 705, the processor of the computing device 102 causes the generated code to be displayed on the display device of computing device 102. In some implementations, the processor of the computing device 102 may transmit the generated code to the medication dispenser 106 to cause the authentication process at the medication dispenser 106 to utilize the newly generated code when the medication dispenser 106 authenticates an entered code and determines whether the medication dispenser 106 should dispense the prescribed amount of the medication.

Figure 8:
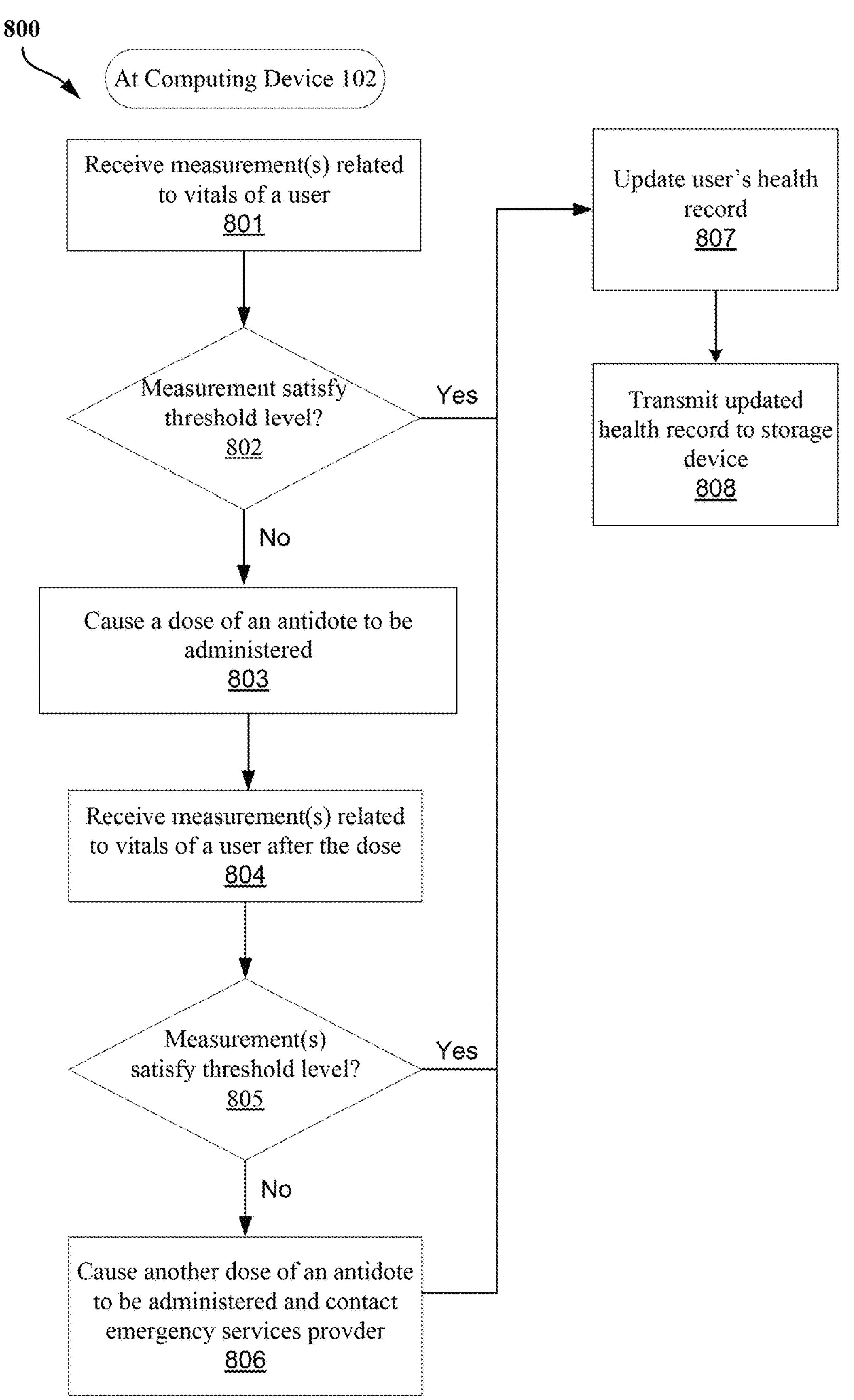
FIG. 8 illustrates a flowchart of an example method for causing an administration of an antidote for an overdose, in accordance with some embodiments of the present disclosure.

Turning now to FIG. 8, there is shown an example method 800 for causing an administration of an antidote for an overdose. The example process may be implemented at a computing device 102, and can be performed using one or more components (e.g., a processor, a memory, and the like) of the computing device 102.

At block 801, the processor of the computing device 102, receives one or more measurements related to the vitals of the user. For example, the computing device 102 may receive the one or more measurements from the health monitoring device 104. At block 802, the processor of the computing device 102, determines whether each of the one or more measurements satisfy a corresponding threshold level. For example, the processor of the computing device 102 may determine whether a received respiratory rate of the user satisfies a threshold respiratory rate level, whether a received heart rate of the user satisfies a threshold heart rate level, and the like. If the processor of the computing device 102 determines that each of the received measurements satisfy their corresponding threshold levels ("Yes" at block 802), then the method 800 proceeds to block 807. At block 807, the processor of the computing device 102 updates a health record and/or a set of health related data with the received measurements, and then, at block 808, the processor of the computing device 102 transmits the updated health record to server computing device 108 for storing the updated health record.

At block 802, if the processor of the computing device 102 determines that a received measurement fails to satisfy a corresponding threshold level ("No" at block 802), then the processor of the computing device 102 determines that the user is overdosing. At block 802, if the processor of the computing device 102 determines that a received measurement fails to satisfy a corresponding threshold level ("No" at block 802), then the method 800 proceeds to block 803. At block 803, the processor of the computing device 102 causes a dose of an antidote to be administered by the health monitoring device 104. For example, the processor of the computing device 102 may transmit a message to the health monitoring device 104 indicating that a dose of an antidote should be administered. In some implementations, the processor of the computing device 102 may contact and/or transmit an alert to an emergency services provider. The processor of the computing device 102 may be configured to determine a geographical location of the user based on a radio component, such as radio navigations system, and the like of the computing device 102, and provide the user's geographical location to the emergency services provider. In some implementations, the processor of the computing device 102 may be configured to determine identifying information of the user, such as hair color, eye color, height, weight, and the like. In some implementations, the identifying information of the user may be stored along with the user profile and/or user identifier on a storage device communicatively coupled to the processor and/or the computing device 102 (e.g., a storage device remotely located from the computing device 102).

At block 804, the processor of the computing device 102 receives one or more measurements related to the vitals of the user after the administration of the dose of antidote. At block 805, the processor of the computing device 102 determines whether the measurements received after the administration of the first dose of antidote satisfy corresponding threshold levels. If the processor of the computing device 102 determines that each of the received measurements satisfy their corresponding threshold levels ("Yes" at block 805), then the method 800 proceeds to block 807. If the processor of the computing device 102 determines that a received measurement fails to satisfy a corresponding threshold level ("No" at block 802), then the method 800 proceeds to block 806. At block 806, the processor of the computing device 102 causes another dose (e.g., a second dose) of the antidote to be administered to the user. In some implementations, in response to causing another dose of the antidote to be administered, the processor of the computing device 102 may be configured to contact and/or transmit an alert to the emergency services provider. The method 800 then proceeds to blocks 807 and 808.

Figure 9:
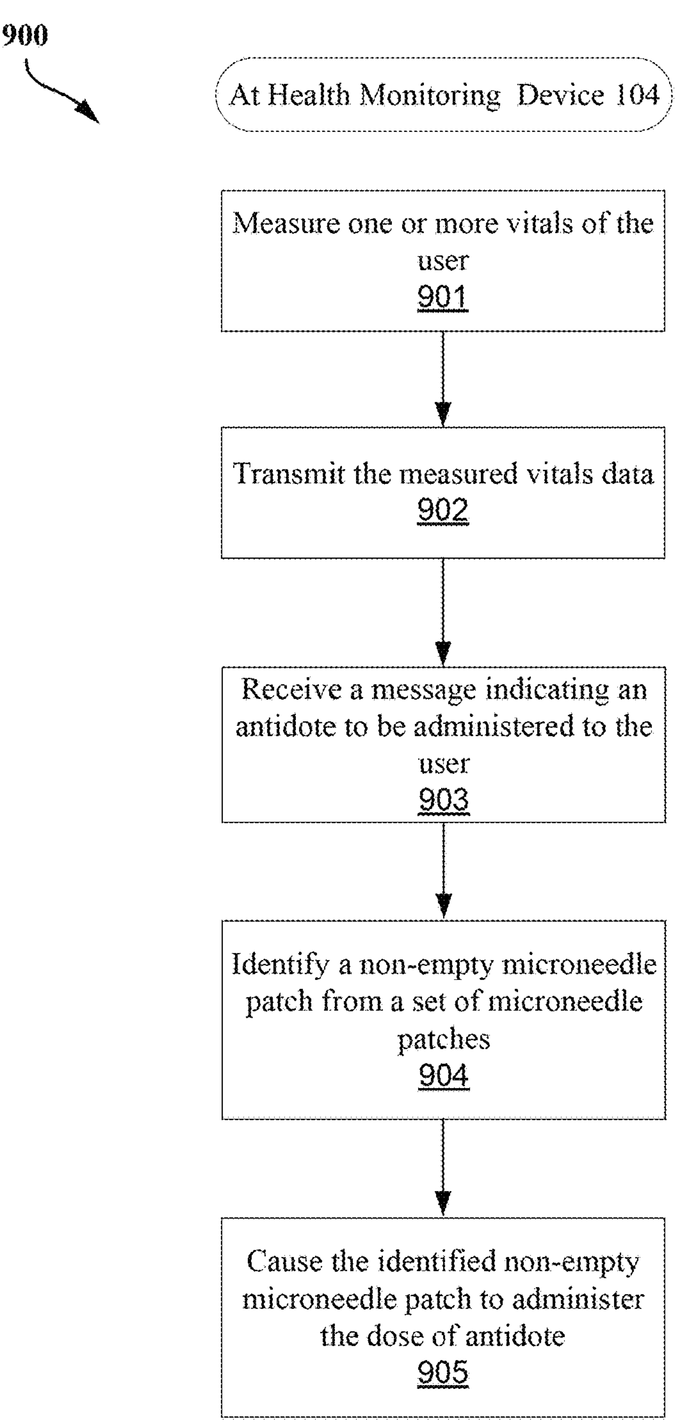
FIG. 9 illustrates a flowchart of an example method for autonomously administering an antidote for an overdose, in accordance with some embodiments of the present disclosure.

Turning now to FIG. 9, there is shown an example method 900 for autonomously administering an antidote for an overdose to a user. The example process may be implemented at a health monitoring device 104, and can be performed using one or more components (e.g., one or more sensors 210, one or more microneedle patches 212, a processor, a memory, and the like) of the health monitoring device 104.

At block 901, one or more sensors 210 of the health monitoring device 104 measures one or more vitals of the user. For example, the one or more sensors 210 may measure a heart rate, respiratory rate, and the like. In some implementations, the one or more sensors 210 may transmit the measured data to a processor of the health monitoring device 104.

At block 902, a processor of the health monitoring device 104 transmits the measured vitals data to the computing device 102. At block 903, the processor of the health monitoring device 104 receives a message from the computing device 102 indicating an antidote to be administered to the user. At block 904, the processor of the health monitoring device 104 identifies a non-empty microneedle patch from a set of microneedle patches of the health monitoring device 104.

In some implementations, after each administration of a dose of antidote, the processor of the health monitoring device 104 may be configured to store and track information related to the microneedle patches used in the administration of the antidote. A microneedle patch may be empty once it administers the stored dose of antidote. In some implementations, the processor of the health monitoring device 104 may be configured to identify non-empty microneedle patches based on the used microneedle patches.

At block 905, the processor of the health monitoring device 104, causes the identified non-empty microneedle patch to administer the dose of the antidote. For example, the processor of the health monitoring device 104 may actuate the non-empty microneedle patch to pierce the skin of the user and deliver the stored antidote into the user.

Figure 10:
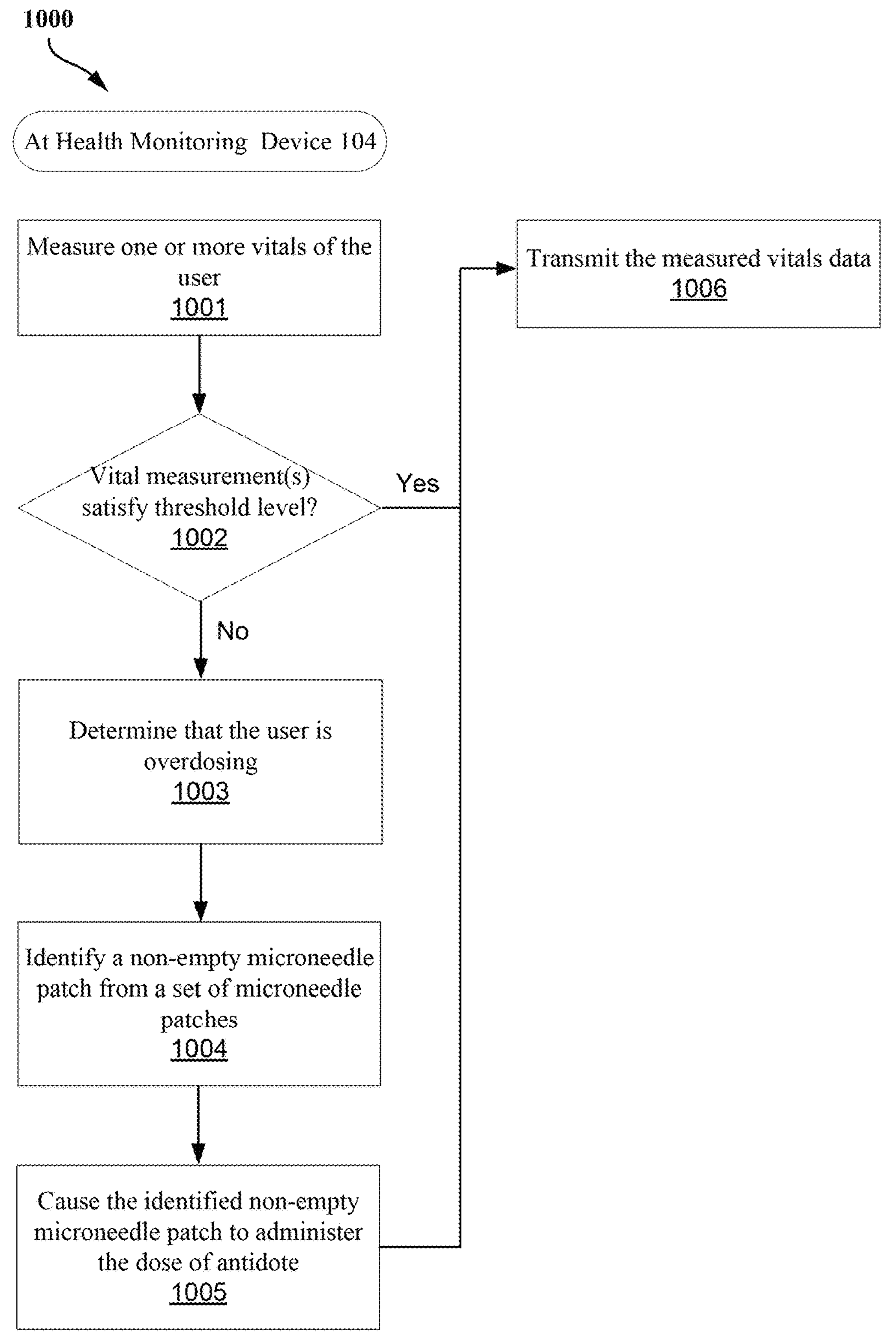
FIG. 10 illustrates a flowchart of an example method for autonomously administering an antidote for an overdose, in accordance with some embodiments of the present disclosure

Turning now to FIG. 10, there is shown an example method 1000 for autonomously administering an antidote for an overdose to a user. The example process may be implemented at a health monitoring device 104, and can be performed using one or more components (e.g., one or more sensors 210, one or more microneedle patches 212, a processor, a memory, and the like) of the health monitoring device 104.

At block 1001, one or more sensors 210 of the health monitoring device 104 may be configured to measure one or more vitals of the user. For example, the one or more sensors 210 may measure a heart rate, respiratory rate, and the like. In some implementations, the one or more sensors 210 may transmit the measured data to a processor of the health monitoring device 104. In some implementations, the one or more sensors 210 may transmit the measured data to a processor of the health monitoring device 104.

At block 1002, if the processor of the health monitoring device 104 determines that the received measurement satisfies a corresponding threshold level ("Yes" at block 1002), then the method 1000 proceeds to block 1006. At block 1006, the processor of the health monitoring device 104 transmits the measured vitals data to the computing device 102.

At block 1002, if the processor of the health monitoring device 104 determines that a received measurement fails to satisfy a corresponding threshold level ("No" at block 1002), then the processor of the health monitoring device 104 determines that the user is overdosing. In some implementations, the processor of the health monitoring device 104 may contact and/or transmit an alert to an emergency services provider.

In some implementations, the processor of the health monitoring device 102 may be configured to transmit a message and/or an instruction to the computing device 102 to cause the computing device 102 to transmit an alert to an emergency services provider. In some implementations, the processor of the health monitoring device 104 may be configured to request geographical location and/or other identifying information of the user from the computing device 102 and transmit the geographical location and/or other identifying information of the user to the emergency services provider when transmitting the alert. In some implementations, the health monitoring device 104 may include one or more radio components, such as radio navigations system, and the like, and the processor of the health monitoring device 104 may be configured to determine a geographical location of the user based on the one or more radio components of the health monitoring device 104, and provide the user's geographical location to the emergency services provider.

At block 1002, if the processor of the health monitoring device 104 determines that a received measurement fails to satisfy a corresponding threshold level ("No" at block 1002), then the method 1000 proceeds to block 1003. At block 1003, the processor of the health monitoring device 104 determines that the user is overdosing.

At block 1004, the processor of the health monitoring device 104 identifies a non-empty microneedle patch from a set of microneedle patches of the health monitoring device 104. In some implementations, after each administration of a dose of antidote, the processor of the health monitoring device 104 may be configured to store and track information related to the microneedle patches used in the administration of the antidote. A microneedle patch may be empty once it administers the stored dose of antidote. In some implementations, the processor of the health monitoring device 104 may be configured to identify non-empty microneedle patches based on the used microneedle patches.

At block 1005, the processor of the health monitoring device 104, causes the identified non-empty microneedle patch to administer the dose of the antidote. For example, the processor of the health monitoring device 104 may actuate the non-empty microneedle patch to pierce the skin of the user and deliver the stored antidote into the user. At block 1006, a processor of the health monitoring device 104 transmits the measured vitals data to the computing device 102.

In some implementations, the processor of the health monitoring device 104 may be configured to receive a health record of the user and/or a set of health related data of the user from a storage device storing the health records and/or health related data of the user. In some implementations, the In some implementations, the processor of the health monitoring device 104 may be configured to update a health record and/or a set of health related data of the user with the one or more of the vitals measurements. In some implementations, the processor of the health monitoring device 104 may be configured to transmit the updated health record to server computing device 108 for storing the updated health record.

Figure 11:
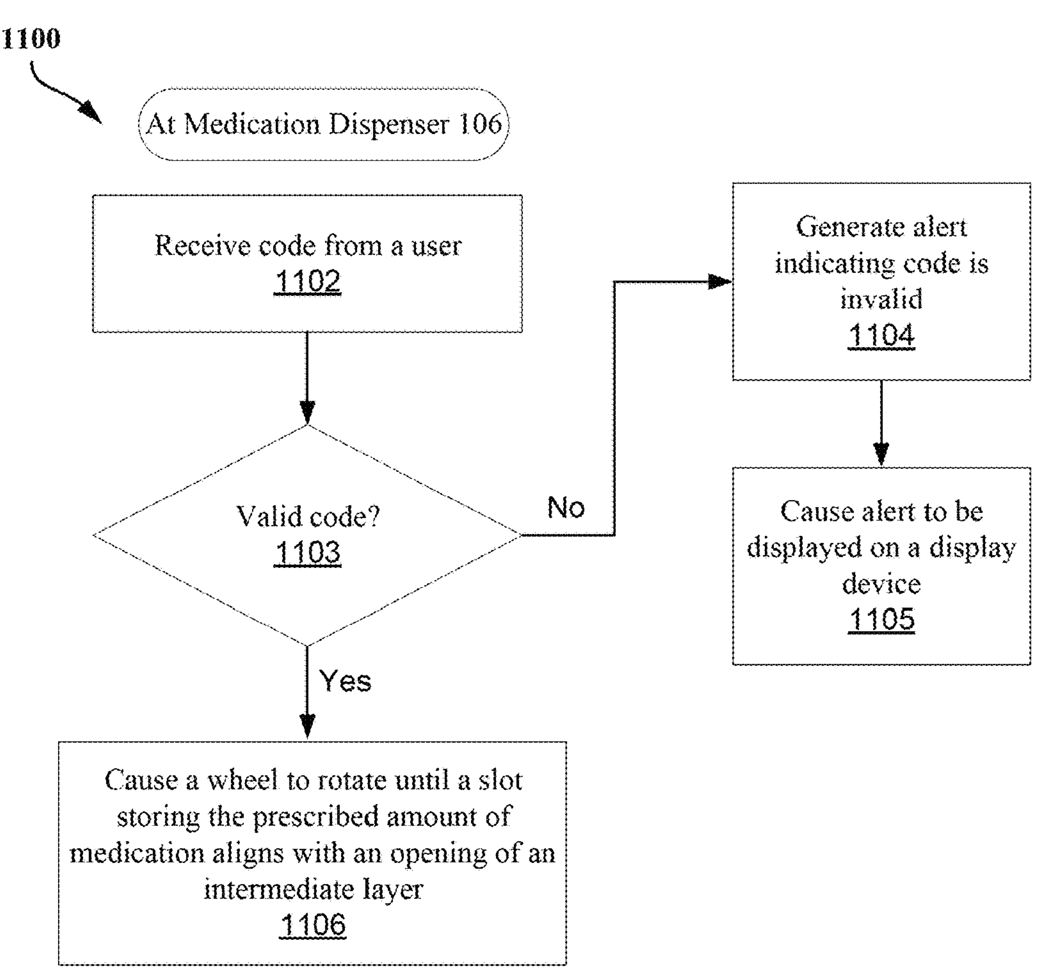
FIG. 11 illustrates a flowchart of an example method for dispensing a prescribed amount of medication to a user, in accordance with some embodiments of the present disclosure.

Turning now to FIG. 11, there is shown an example method 1100 for dispensing a prescribed amount of medication to a user. The example process may be implemented at a medication dispenser device 106, and can be performed using one or more components (e.g., a wheel 301 a processor, a memory, and the like) of the health monitoring device 106.

At block 1102, a processor of the medication dispenser 106 receives, a code generated by computing device 102 from a user. For example, a user may provide the code to medication dispenser 106 via the keypad 306 of the medication dispenser 106, and, as described above, the keypad 306 may transmit the user entered code to the processor of the medication dispenser 106. At block 1103, the processor of the medication dispenser 106 determines whether the received code is a valid code. For example, the processor of the medication dispenser 106 may retrieve the generated code received from the computing device 102 and compare the user provided code with the code received from the computing device 102 and determine that the code is a valid code if there is a match between the two.

If the processor determines that the code received from the user is not a valid code ("No" at block 1103), then the method 1100 proceeds to block 1104. At block 1104, the processor generates an alert that indicates that the code is an invalid code, and at block 1105 causes the alert to be displayed on a display device of the medication dispenser 106. For example, the keypad 306 may include a display device and the invalid code alert may be displayed on a display device of the keypad 306. If the processor determines that the code received from the user is a valid code ("Yes" at block 1103), then the method 1100 proceeds to block 1106.

At block 1106, the processor of the medication dispenser 106 causes a wheel 302 of the medication dispenser 106 to rotate until a slot storing the prescribed amount of medication aligns with an opening of an intermediate layer 303 of the medication dispenser 106. As described above, the processor of the medication dispenser 106 may turn a motor of the medication dispenser 106 and the motor of the medication dispenser 106 may rotate the wheel 303 until a slot of the wheel 303 aligns with the opening of the intermediate layer 303, which causes the prescribed medication stored in the slot 308 to be dispensed into a tray 305 of the medication dispenser 106. This allows the user to retrieve the prescribed medication from the tray 305 of the medication dispenser.

With respect to FIG. 12, a block diagram illustrates an embodiment of a processing system 1200. The processing system 1200 may comprise at least one or more processors associated with at least computing system. For example, referring to FIGS. 1-11, the processing system 1200 may be an embodiment of a processing system of at least one of the computing device 102, health monitoring device 104, medication dispenser 106, server computing device 108.

The system 1200 may include various types of machine-readable media and interfaces. As illustrated, the system 1200 includes at least one interconnect 1220 (e.g., at least one bus), a permanent storage device 1222, random-access memory (RAM) 1224, at least one controller interface(s) 1226, read-only memory (ROM) 1228, at least one processor(s) 1230, and a network component 1232.

The interconnect 1220 may communicatively connect components and/or devices that are collocated with the system 1200, such as internal components and/or internal devices within a housing of the system 1200. For example, the interconnect 1220 may communicatively connect the processor(s) 1230 with the permanent storage device 1222, RAM 1224, and/or ROM 1228. The processor(s) 1230 may be configured to access and load computer-executable instructions from at least one of the permanent storage device 1222, RAM 1224, and/or ROM 1228.

The permanent storage 1222 may be non-volatile memory that stores instructions and data, independent of the power state (e.g., on or off) of the system 1200. For example, the permanent storage 1222 may be a hard disk, flash drive, or another read/write memory device.

ROM 1228 may store static instructions enabling basic functionality of the system 1200, as well as the components therein. For example, ROM 1228 may store instructions for the processor(s) 1230 to execute a set of processes associated with robot of at least a portion of a vehicle, for example, as described with respect to one or more of the robots, above. Examples of ROM 1228 may include erasable programmable ROM (EPROM) or electrically EPROM (EEPROM), compact disc ROM (CD-ROM) or other optical disk storage, magnetic disk storage or other magnetic storage devices, and/or another computer-accessible and computer-readable medium that may store program code as instructions and/or data structures.

RAM 1224 may include volatile read/write memory. RAM 1224 may store computer-executable instructions associated with runtime operation(s) by the processor(s) 1230. In addition, RAM 1224 may store real-time data captured during the operations as described with respect to one or more of FIGS. 1 through 11, above, for example.

The processor(s) 1230 may be implemented with one or more general-purpose and/or special-purpose processors. Examples of general-purpose and/or special-purpose processors may include microprocessors, microcontrollers, DSP processors, and/or any other suitable circuitry configured to execute instructions loaded from at least one of the permanent storage device 1222, RAM 1224, and/or ROM 1228. Alternatively or additionally, the processor(s) 1230 may be implemented as dedicated hardware, such as at least one field programmable gate array (FPGA), at least one programmable logic device (PLD), at least one controller, at least one state machine, a set of logic gates, at least one discrete hardware component, or any other suitable circuitry and/or combination thereof.

The interconnect 1220 may further communicatively connect the system 1200 with one or more controller interface(s) 1226. The controller interface(s) 1226 may communicatively connect the system 1200 with various circuitry associated with one or more components of the computing devices described above with respect to FIGS. 1-11 and/or other computing devices, for example, during the operations described above with respect to FIGS. 1-11. Instructions executed by the processor(s) 1230 may cause instructions to be communicated with one or more components of the computing devices described above with respect to FIGS. 1-11 through the controller interface(s) 1226. For example, instructions executed by the processor(s) 1230 may cause signals to be sent through the controller interface (s) 1226 to circuitry and/or other components of the computing device 102, health monitoring device 104, medication dispenser 106, server computing device 108, and/or the like, described above with respect to FIGS. 1-11.

In some embodiments, the system 1200 may include a network component 1232. The network component 1232 may be configured to communicate over a network, for example, in order to transmit and/or receive instructions associated with assembly of at least a portion of a vehicle. Instructions communicated over a network through the network component 1232 may include instructions associated with one or more operations described above with respect to FIGS. 1-11. Examples of a network through which the network component 1232 may communicate may include peer to peer networks, such as a Bluetooth (BT) network, a local area network (LAN), a wide area network (WAN), the Internet, an intranet, or another wired or wireless network.

It is understood that the specific order or hierarchy of blocks in the processes/flowcharts disclosed is an illustration of example approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Terms such as "if" "when," and "while" should be interpreted to mean "under the condition that" rather than imply an immediate temporal relationship or reaction. That is, these phrases, e.g., "when," do not imply an immediate action in response to or during the occurrence of an action, but simply imply that if a condition is met then an action will occur, but without requiring a specific or immediate time constraint for the action to occur. The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed as a means plus function unless the element is expressly recited using the phrase "means for."

What is claimed is:

1. A health monitoring device comprising:

a band;

one or more sensors;

a stored overdose prevention medication;

a plurality of microneedle patches;

a memory; and at least one processor coupled to the memory and configured to:

receive, from the one or more sensors, one or more measurements related to one or more vitals of a user;

perform, based on the one or more measurements, autonomous administration via injection of a first dose of the stored overdose prevention medication to the user by one or more microneedle patches of the plurality of microneedle patches, wherein the one or more vitals of the user are encrypted health data; and track information relating to the one or more microneedle patches for presentation, wherein the tracked information includes a current level of overdose prevention medication of each of the one or more microneedle patches after the autonomous administration;

wherein at least one of the plurality of microneedle patches is removable and replaceable;

wherein the one or more sensors and the plurality of microneedle patches are located on a side of the band; and wherein the at least one processor is configured to perform the autonomous administration via injection of the first dose of the stored overdose prevention medication to the user by:

identifying a non-empty microneedle patch from the plurality of microneedle patches of the health monitoring device; and perform the autonomous administration, via the identified non-empty microneedle patch, of the first dose of the stored overdose prevention medication to the user.

2. The health monitoring device of claim 1, wherein the at least one processor is configured to perform the autonomous administration of the first dose of the stored overdose prevention medication to the user by:

determining whether the one or more measurements is above a corresponding threshold measurement level; and in response to determining that the one or more measurements is above the threshold, administering the first dose of the stored overdose prevention medication.

3. The health monitoring device of claim 1, wherein the at least one processor is configured to:

transmit the one or more measurements to a computing device associated with the user.

4. The health monitoring device of claim 1, wherein the at least one processor is configured to:

receive, in response to transmission of the one or more measurements, an instruction associated with the administration of the first dose of the stored overdose prevention medication to the user.

5. The health monitoring device of claim 4, wherein the at least one processor is configured to perform the autonomous administration of the first dose of the stored overdose prevention medication to the user in response to the received instruction indicating administration of the first dose of the stored overdose prevention medication to the user.

6. The health monitoring device of claim 1, wherein performing the autonomous administration via injection of the first dose of the stored overdose prevention medication by one or more microneedle patches of the plurality of microneedle patches further comprises:

actuating the one or more microneedle patches of the plurality of microneedle patches to pierce a portion of body of the user.

7. The health monitoring device of claim 1, wherein the at least one processor is configured to transmit an alert an emergency service provider.

8. A computing device comprising:

a display device;

a memory; and at least one processor coupled to the memory and configured to:

determine, based on received credentials, whether a user is a valid user by comparing the received credentials with stored credentials;

in response to determination that the user is a valid user, generate a code to unlock a medication dispenser;

cause the generated code to be displayed on the display device;

transmit, to a server, one or more encrypted measurements related to one or more vitals of the user, wherein the stored credentials are associated with encrypted health data;

receive, after a first dose of overdose prevention medication is caused to be administered to the user, a second measurement related to the one or more vitals of the user;

cause, based on the second measurement and a corresponding threshold level of the one or more vitals, autonomous administration of a second dose of the overdose prevention medication to the user, wherein the second dose is caused to be autonomously administered from a different microneedle patch than the first dose; and track information relating to the different microneedle patch for presentation, wherein the tracked information includes a current level of overdose prevention medication of the different microneedle patch after the autonomous administration of the second dose.

9. The computing device of claim 8, wherein the at least one processor is configured to generate the code to unlock the medication dispenser by:

determining whether a first time satisfies a medication dispensation time;

in response to determining that the first time satisfies the medication dispensation time, generating the code to unlock the medication dispenser; and in response to determining that the first time fails to satisfy the medication dispensation time, causing an alert to be displayed to the display device, wherein the alert indicates that the first time is not a time for medication consumption.

10. The computing device of claim 9, wherein the at least one processor is configured to:

when the first time fails to satisfy the medication dispensation time, determine whether a medication attempt indicator satisfies a corresponding threshold number of medication attempts; and in response to determining that the medication attempt indicator satisfies the corresponding threshold number of medication attempts, transmit an alert to a computing device associated with a clinician, wherein the clinician is associated with the user.

11. The computing device of claim 8, wherein medication dispensation time is a range of time periods.

12. The computing device of claim 8, wherein the at least one processor is configured to:

receive a first measurement related to the one or more vitals of the user; and cause, based on the first measurement, administration of the first dose of the overdose prevention medication to the user.

13. The computing device of claim 11, wherein the at least one processor is configured to cause the administration of the first dose of the overdose prevention medication to the user by:

determining, based on the measurement and the corresponding threshold level of the one or more vitals, whether the user is overdosing; and in response to determining that the user is overdosing, causing autonomous administration of the first dose of the overdose prevention medication to the user.

14. The computing device of claim 8, wherein the at least one processor is configured to:

receive one or more measurements related to the one or more vitals of the user from a health device;

update, based on the one or more measurements, a health record of the user; and cause the health record to be displayed on a second display device to a physician associated with the user.

15. The health monitoring device of claim 1, wherein the band is a bracelet.

* * * * *